(12) United States Patent
Wieczorek

(10) Patent No.: US 7,241,279 B1
(45) Date of Patent: Jul. 10, 2007

(54) HAND-OPERATED SQUEEZABLE EYE WASHER

(76) Inventor: Mark Donald Wieczorek, 3421 Yonge St., San Diego, CA (US) 92106

( * ) Notice: Subject to any disclaimer, the term of this patent is extended or adjusted under 35 U.S.C. 154(b) by 66 days.

(21) Appl. No.: 11/404,365

(22) Filed: Apr. 14, 2006

(51) Int. Cl.
*A61M 35/00* (2006.01)
(52) U.S. Cl. .................. 604/295; 604/294; 604/299
(58) Field of Classification Search .......... 604/19, 604/521, 212, 289, 294–300
See application file for complete search history.

(56) References Cited

U.S. PATENT DOCUMENTS

D248,448 S 7/1978 McClure et al.
4,784,652 A 11/1988 Wikstrom
6,385,794 B1 * 5/2002 Miedzius et al. .............. 4/620
6,913,598 B2 7/2005 Tangri

OTHER PUBLICATIONS

Eye Wash Shower Bottle, published at http://www.seton.net.au/product_detail.cfm/hurl/Masterno=Z0064W/product_deta.

* cited by examiner

*Primary Examiner*—Michele Kidwell
(74) *Attorney, Agent, or Firm*—Mayer & Williams PC; Mark D. Wieczorek, Esq.

(57) ABSTRACT

A portable eye washer is described including a bladder, which may be disposable, filled with an eye-washing solution such as water or a solution specially-designed for cleaning eyes. The bladder may be made of rubber, a thin plastic, or other material so long as the bladder material is generally not permeable to the eye washing solution.

20 Claims, 1 Drawing Sheet

HAND-OPERATED SQUEEZABLE EYE WASHER

FIELD OF THE INVENTION

This invention relates to portable eye washers for use in cleansing eyes in situations where undesired material or fluids impinge on an eye.

BACKGROUND OF THE INVENTION

In various environments, such as chemistry labs, workshops of various types, and other dangerous workplaces, materials or fluids may undesiredly impinge on the eye. For example, in a wood shop, wood shavings may be thrown off of motorized saws and impinge on the eye, especially when the operator fails to wear appropriate safety eyewear. In chemistry labs or other workplaces where chemicals are manipulated, occasional splashing of fluids may also result in fluid impingement on an operator's eyes.

Prior eye washing devices are typically in the nature of modified faucets. Such devices often have two nozzles facing substantially upward or along a curve curving substantially upward and separated by about the distance between a typical operator's eyes. But these devices are not portable as they require a piped water supply.

Other such devices employ cup-and-fluid-container combinations where eye washing fluid is provided with a cup that is specially designed for eye washing.

SUMMARY OF THE INVENTION

The present invention, in one aspect, is directed to a portable eye washer including a bladder, which may be disposable, filled with an eye-washing solution such as water or a solution specially-designed for cleaning eyes. The bladder may be made of rubber, a thin plastic, or other material so long as the bladder material is generally not permeable to water.

Integral with or attached to the bladder are at least two nozzles.

Implementations of the invention may include one or more of the following. The bladder may be disposable More than one nozzle may be disposed on the bladder to accommodate operators with vastly differing distances between their eyes. For example, a child and an adult may use the same portable eye-washing device.

In one aspect, the invention is directed to a device for washing eyes, including a bladder having sufficient flexibility such that when squeezed can compress to increase the pressure on contents within the bladder, and at least two nozzles in pressure communication with the bladder, each nozzle having at least one discharge hole defined therein, such that when the bladder is squeezed a sufficient amount, and the pressure on the contents of the bladder thus subsequently increased a sufficient amount, at least a portion of the contents of the bladder are forced through the discharge holes. The at least two nozzles are configured such that a portion of the contents of the bladder, when forced through the discharge holes, are between about 5 and 15 centimeters apart at a distance of between about 1 and 30 centimeters from the discharge holes.

Implementations of the invention may include one or more of the following. The bladder and/or nozzles may be made of a rubber-based, plastic, or polymer-based material. The discharge holes may have a diameter of between about 0.1 and 2 mm. The nozzles may be configured to be substantially closed when the pressure within the bladder is below a predetermined maximum and to be substantially open when the pressure within the bladder is above the predetermined maximum. The nozzles may further comprise a cover, where the cover is configured to be substantially closed when the pressure within the bladder is below a predetermined maximum and substantially open when the pressure within the bladder is above the predetermined maximum. The cover may also be a breakaway cover, where the cover is configured to break away when the pressure within the bladder exceeds a predetermined maximum. The breakaway cover may be affixed to the nozzle along a portion of its circumference such that the breakaway cover remains affixed to the nozzle at a location adjacent the discharge hole following its breakaway. The portion of its circumference may be less than 180 degrees of circumference. An eye wash solution may be disposed in the bladder, such as a water-based solution, water, or a saline-based solution.

In another aspect, the invention is directed to a method for making a portable eye wash device, including forming a hollow bladder; forming or mounting at least two nozzles in pressure communication with the hollow bladder; filling the hollow bladder with an eye wash solution; such that when the bladder is squeezed a sufficient amount, and the pressure on the eye wash solution in the bladder subsequently increased a sufficient amount, at least a portion of the eye wash solution in the bladder is forced through the discharge holes; and such that the at least two nozzles are configured such that a portion of the eye wash solution in the bladder, when forced through the discharge holes, is between about 5 and 15 centimeters apart at a distance of between about 1 and 30 centimeters from the discharge holes.

Implementations of the invention may include one or more of the following. The eye wash solution may be selected from the group consisting of water-based solutions, water, and saline solutions. The method may further comprise mounting a breakaway cover on the nozzles, substantially closing off the discharge holes, until removal of the breakaway cover occurs. The method may further comprise affixedly attaching the breakaway cover along a portion of its circumference to the nozzle such that the breakaway cover remains attached to the nozzle following removal from covering the discharge hole.

Advantages of the invention may include one or more of the following. Certain embodiments are portable and easy-to-operate. The fluid pressure impinging on the operator's eyes is conveniently controllable by the user. The device may be refillable or may be completely disposable for sterility. Other advantages and features of the invention may be seen by reference to the below description, including the figures and claims.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In the following description, the term "pressure communication" is used to describe a situation between two points in a flow or in a standing fluid. If pressure is applied at one point, the second point will eventually feel effects of the pressure if the two points are in pressure communication. Any number of valves or elements may be disposed between the two points, and the two points may still be in pressure communication if the above test is met. For example, for a standing fluid in a pipe, any number of pipe fittings may be disposed between two pipes and, so long as an open path is maintained, points in the respective pipes may still be in pressure communication.

Figure 1:
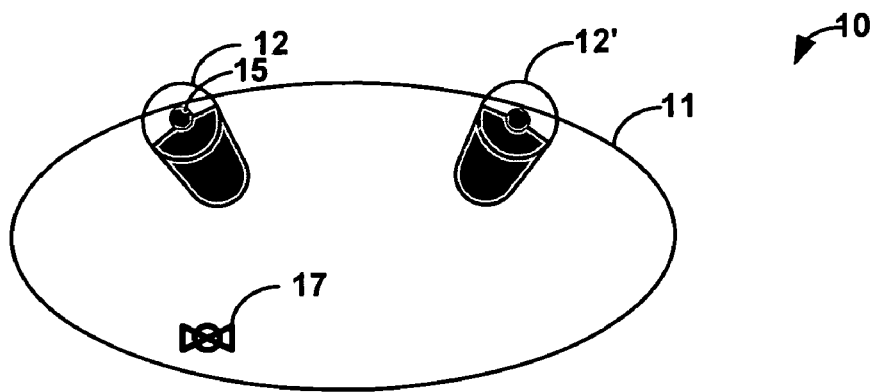
FIG. 1 shows a perspective view of an embodiment of a portable eye-washing device according to the present invention.

The present invention will now be described in greater detail by way of the following description of exemplary embodiments and variations of the systems and methods of the present invention. Referring to FIG. 1, a portable eye-washing device 10 is shown having a bladder 11 and nozzles 12 and 12'. The bladder 11 may be made of, e.g., rubber, thin plastic, or any other flexible material that is relatively impermeable to liquids at normal pressures. The bladder should be flexible enough to be easily squeezed by the operator so as to cause the eye-washing fluid within to discharge from the nozzles 12 and 12'.

The nozzles 12 and 12' may be formed integral with the bladder 11 or may be mounted thereon. For example, the nozzles 12 and 12' may be made of the same rubber constituting the bladder. The nozzles 12 and 12' should be separated and angled such that flows of liquid discharging therefrom are separated by about the distance of the operator's eyes. The nozzles are formed with discharge holes 15 at their upper extremity, and the diameter of the discharge holes may be chosen such that the resultant discharge stream, given the pressure of a typical operator's squeeze, results in an appropriate force and stream width for the eye wash solution. Without the force of a typical operator's squeeze, the discharge hole may close on itself without additional force due to the resilient material constituting the nozzle.

Any type of eye washing liquid may be employed, including water, saline solutions, eye moisturizers, and others as are known, with the only requirement being that the liquid be chosen such that it does not adversely react with the material of the bladder.

Figure 2:
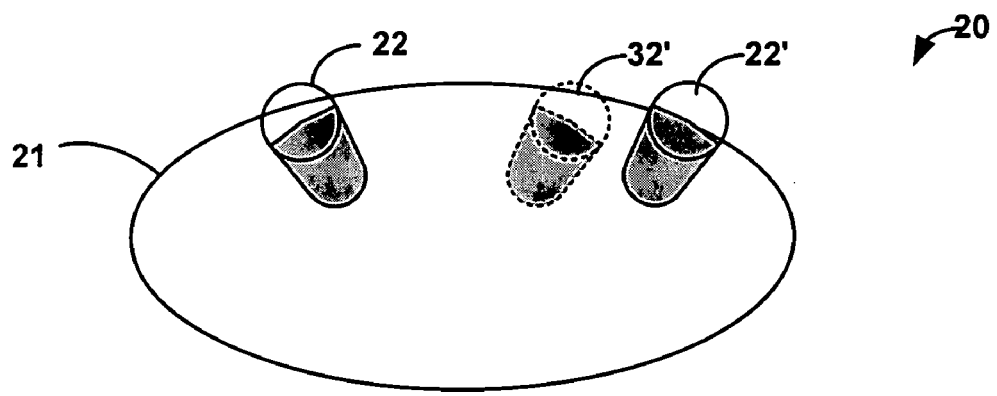
FIG. 2 shows a perspective view of another embodiment of a portable eye-washing device according to the present invention.

In a related embodiment, shown in FIG. 2, a device 20 has greater than two nozzles, e.g., nozzles 22, 22', and 32', which are disposed on a bladder 21. Generally the multiple nozzles may be aligned along a single line. In this embodiment, operators having differing distances between their eyes may be accommodated. The unused nozzles may be prevented from discharging by the operator squeezing the unused nozzles so that fluid cannot discharge from the same.

Figure 3:
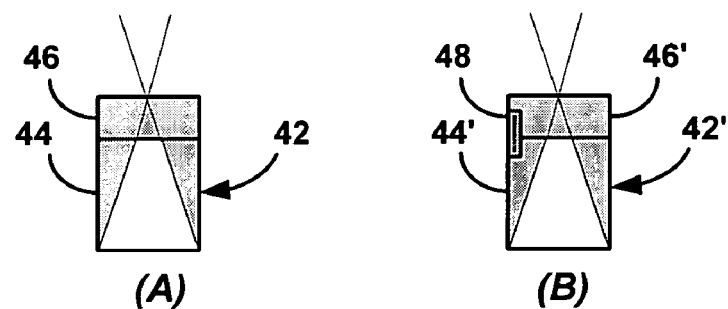
FIGS. 3(A) and (B) show side schematic view of nozzle structures according to embodiments of the present invention.

In the above embodiments, the bladder need not be completely filled with the eye-washing fluid. Rather, the force of the operator squeezing the bladder impels the fluid out of the nozzles. In an alternative embodiment, shown in FIG. 3, the portable eye-washing device may be disposed such that fluid is even more readily available to discharge out of the device. In this embodiment, the bladder may be substantially filled with the eye-washing fluid. Referring to FIG. 3(A), a cover 46 is disposed over a discharge portion 44 of a nozzle 42 so that the fluid does not inadvertently discharge from the nozzles before desired. The cover may be a thin rubber coating over the discharge hole of the nozzle. The cover may be a breakaway cover. In particular, the cover may be such that the area of the cover directly over the nozzle's discharge hole may be made especially thin so that operator force on the bladder increases the pressure impinging on the thin area of the cover to a value greater than that required to cause a hole to form in the thin area of the cover. After a hole is formed, the resulting hole forms its own nozzle action on the fluid discharging from the bladder. In other words, the fluid sprays forth from the resulting hole in such as way as to cleanse the eyes of the operator. In a related embodiment, shown in FIG. 3(B), a cover 46' is disposed over a discharge portion 44' of a nozzle 42' so that the fluid does not inadvertently discharge from the nozzles before desired. The cover 46' is bonded strongly on one side via bond 48, so that when the cover breaks away, the cover 46' continues to be attached on one side. This embodiment has the advantage that no part of the cover may accidentally fly up into the operator's eyes.

While the device may often be disposable, a valve 17 may be disposed to allow the same to be refilled.

While the device and method have been described largely in the context of emergency eye treatments, it should be noted that the device may be used for general eye cleaning, such as is desired, e.g., following contact lens removal, etc.

Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The invention claimed is:

1. A device for washing eyes, comprising:
   a. A bladder having sufficient flexibility such that when squeezed can compress to increase the pressure on contents within the bladder; and
   b. At least two nozzles in pressure communication with the bladder, each nozzle having at least one discharge hole defined therein, such that when the bladder is squeezed a sufficient amount, and the pressure on the contents of the bladder subsequently increased a sufficient amount, at least a portion of the contents of the bladder are forced through the discharge holes;
   c. Such that the at least two nozzles are configured such that a portion of the contents of the bladder, when forced through the discharge holes, are between about 5 and 15 centimeters apart at a distance of between about 1 and 30 centimeters from the discharge holes.

2. The device of claim 1, wherein the bladder is made of a rubber-based material.

3. The device of claim 1, wherein the nozzles are made of a rubber-based material.

4. The device of claim 1, wherein the bladder and nozzles are made of a plastic material.

5. The device of claim 1, wherein the bladder and nozzles are made of polymer-based materials.

6. The device of claim 1, wherein the discharge holes have a diameter of between about 0.1 and 2 mm.

7. The device of claim 1, wherein the nozzles are configured to be substantially closed when the pressure within the bladder is below a predetermined maximum and to be substantially open when the pressure within the bladder is above the predetermined maximum.

8. The device of claim 1, wherein the nozzles further comprise a cover, and wherein the cover is configured to be substantially closed when the pressure within the bladder is below a predetermined maximum and to be substantially open when the pressure within the bladder is above the predetermined maximum.

9. The device of claim 8, wherein the cover is a breakaway cover, and wherein the cover is configured to break away when the pressure within the bladder exceeds a predetermined maximum.

10. The device of claim 9, wherein the breakaway cover is affixed to the nozzle along a portion of its circumference such that the breakaway cover remains affixed to the nozzle at a location adjacent the discharge hole following its breakaway.

11. The device of claim 10, wherein the portion of its circumference is less than 180 degrees of circumference.

12. The device of claim 1, further comprising an eye wash solution disposed in the bladder.

13. The device of claim 12, wherein the eye wash solution is selected from the group consisting of water-based solutions, water, and saline solutions.

14. A method for making a portable eye wash device, comprising:
   a. Forming a hollow bladder;
   b. Forming at least two nozzles in pressure communication with the hollow bladder;
   c. Filling the hollow bladder with an eye wash solution;
   d. such that when the bladder is squeezed a sufficient amount, and the pressure on the eye wash solution in the bladder subsequently increased a sufficient amount, at least a portion of the eye wash solution in the bladder is forced through the discharge holes;
   e. Such that the at least two nozzles are configured such that a portion of the eye wash solution in the bladder, when forced through the discharge holes, is between about 5 and 15 centimeters apart at a distance of between about 1 and 30 centimeters from the discharge holes.

15. The method of claim 14, wherein the eye wash solution is selected from the group consisting of water-based solutions, water, and saline solutions.

16. The method of claim 14, further comprising mounting a breakaway cover on the nozzles, substantially closing off the discharge holes, until removal of the breakaway cover occurs.

17. The method of claim 16, further comprising affixedly attaching the breakaway cover along a portion of its circumference to the nozzle such that the breakaway cover remains attached to the nozzle following removal from covering the discharge hole.

18. A method for making a portable eye wash device, comprising:
   a. Forming a hollow bladder;
   b. mounting at least two nozzles on the hollow bladder such that the at least two nozzles are in pressure communication with the hollow bladder;
   c. Filling the hollow bladder with an eye wash solution;
   d. such that when the bladder is squeezed a sufficient amount, and the pressure on the eye wash solution in the bladder subsequently increased a sufficient amount, at least a portion of the eye wash solution in the bladder is forced through the discharge holes;
   e. Such that the at least two nozzles are configured such that a portion of the eye wash solution in the bladder, when forced through the discharge holes, is between about 5 and 15 centimeters apart at a distance of between about 1 and 30 centimeters from the discharge holes.

19. The method of claim 18, wherein the eye wash solution is selected from the group consisting of water-based solutions, water, and saline solutions.

20. The method of claim 14, further comprising mounting a breakaway cover on the nozzles, substantially closing off the discharge holes, until removal of the breakaway cover occurs.

* * * * *